United States Patent
Heismann et al.

(10) Patent No.: US 7,851,765 B2
(45) Date of Patent: Dec. 14, 2010

(54) DEVICE AND METHOD FOR COOLING AN X-RADIATION DETECTOR

(75) Inventors: Björn Heismann, Erlangen (DE); Gunter Müller, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 436 days.

(21) Appl. No.: 11/802,891

(22) Filed: May 25, 2007

(65) Prior Publication Data

US 2007/0284535 A1    Dec. 13, 2007

(30) Foreign Application Priority Data

May 29, 2006   (DE) ................ 10 2006 024 972

(51) Int. Cl.
 *G01T 1/24*   (2006.01)
(52) U.S. Cl. ................................. 250/370.15
(58) Field of Classification Search ............ 250/370.09, 250/370.15; 378/199
See application file for complete search history.

(56) References Cited

U.S. PATENT DOCUMENTS

| | | | |
|---|---|---|---|
| 4,831,639 A | 5/1989 | Harke | |
| 4,969,167 A | 11/1990 | Zupancic et al. | |
| 5,761,269 A | 6/1998 | Sugihara et al. | |
| 6,411,672 B1 | 6/2002 | Sasaki et al. | |
| 6,909,775 B2 | 6/2005 | Ray et al. | |
| 2004/0022351 A1 | 2/2004 | Lacey et al. | |
| 2004/0071259 A1 | 4/2004 | Lacey et al. | |
| 2004/0228450 A1* | 11/2004 | Mueller | 378/199 |
| 2006/0097174 A1* | 5/2006 | Hoge | 250/363.1 |
| 2006/0126782 A1 | 6/2006 | Pohan et al. | |

FOREIGN PATENT DOCUMENTS

| | | |
|---|---|---|
| DE | 197 04 338 A1 | 8/1998 |
| DE | 19704338 A1 * | 8/1998 |
| DE | 102004055752 A1 | 6/2006 |
| EP | 0182040 B1 | 11/1988 |
| EP | 0296339 A1 | 12/1988 |
| WO | WO 03/046610 A1 | 6/2003 |

OTHER PUBLICATIONS

German Office Action (dated Jan. 2, 2007) for German Patent Application DE 10 2004 055 752.
German Office Action (dated Oct. 18, 2007) for counterpart German Patent Application No. 10 2006 024 972.0-52.

* cited by examiner

*Primary Examiner*—David P Porta
*Assistant Examiner*—Marcus H Taningco
(74) *Attorney, Agent, or Firm*—Harness, Dickey & Pierce, P.L.C.

(57) ABSTRACT

A cooling device is disclosed for a radiation detector including a detector surface and a plurality of collimator plates arranged in the direction of X-radiation before the detector surface. In order to produce the cooling device of at least one embodiment, the collimator plates are designed and/or the cooling device includes a ventilation device which is designed, so that the space between the collimator plates is at least partially exposed to a cooling air flow in order to cool the radiation detector. A corresponding method for cooling an X-radiation detector is furthermore described in at least one additional embodiment.

30 Claims, 4 Drawing Sheets

DEVICE AND METHOD FOR COOLING AN X-RADIATION DETECTOR

PRIORITY STATEMENT

The present application hereby claims priority under 35 U.S.C. §119 on German patent application number DE 10 2006 024 972.0 filed May 29, 2006, the entire contents of which is hereby incorporated herein by reference.

FIELD

Embodiments of the invention generally relate to a cooling device for an X-radiation detector and/or to a cooling system for an X-radiation detector arrangement. Embodiments of the invention furthermore generally relate to a computer tomography system having a cooling system. Embodiments of the invention also generally relate to a method for cooling an X-radiation detector.

BACKGROUND

In medical practice, imaging systems play an important role in the examination of patients. The representations of the patient's internal organs and structures generated by imaging systems are used to diagnose diseases, to plan operations, to carry out operations or to prepare for therapeutic measures. Besides systems which generate the patient image data by applying magnetic fields (for example magnetic resonance tomographs) or with the aid of ultrasound waves, imaging systems which use X-radiation are particularly important. These systems include for example angiography devices, mammography devices and special computer tomography systems.

In a typical arrangement of an imaging system based on X-radiation, an X-ray source lies on one side of a patient and an X-radiation detector lies on the other side of the patient. The detector is used to determine how strongly the X-radiation emitted by the source is attenuated when it passes through the patient's exposed body region. With the aid of the spatial dependency of this attenuation, image data can be generated.

A typical X-radiation detector converts the strength of the X-ray beam into an electrical signal, which can be fed to an image processing system. Conventional embodiments of a corresponding detector are radiation converters, for example so-called scintillation crystals with a downstream image recorder, for example a photodiode array.

In the scintillation crystal, the incident X-radiation causes the creation of light pulses owing to the photoeffect. The generated light pulses are then converted by the photodiode array into electrical signals, which carry information about the strength of the X-radiation. For example, the amplitude of an analog electrical signal might describe the strength of the X-radiation. Furthermore, detectors with integrated analog-digital converters, which output digital electrical signals to describe the radiation strength, are now also customary.

X-radiation detectors are conventionally supplemented with so-called collimators or collimator plates, which are aligned in the direction of the X-radiation. Scattered rays, which deviate from this direction, are absorbed by the collimator plates. Image artifacts, which result from scattering, can thereby be reduced. Such collimator plates are, for example, made from lead or tungsten.

A fundamental problem with X-radiation detectors is that the individual components generate heat during operation of the detector, which can compromise the function of the detector per se or even prevent it from functioning. For example, the accuracy of the analog-digital conversion can deteriorate at operating temperatures which are too high. Conventional maximum tolerable temperatures are about 60° C. in this case.

This fundamental problem has repercussions especially in computer tomography systems. In order to reduce image recording times and increase the image resolution in computer tomography systems, detector arrays are used with a multiplicity of radiation detectors which are often operated simultaneously. In current systems, a heat loss with a power of 1000 W can readily occur in the detectors, which without further measures could greatly compromise or prevent operation of the detectors. Accordingly, it is necessary to cool the X-ray detectors during operation.

The use of conventional cooling systems, for example cooling with the aid of a coolant and a heat exchanger, however, is elaborate and uneconomical for example for a computer tomography system owing to the large number of detectors. Furthermore, many computer tomography systems use detectors mounted in a mobile fashion, which surround the patient in the shape of a circle. This makes cooling with a liquid even more difficult.

Another already existing embodiment of detector cooling in computer tomography systems uses fans, which create an air flow on the other side of the detector from the X-ray source. The cooling power achievable in this way, however, is insufficient for larger detector arrangements since the thermal conduction resistances from the heat sources in the detector are too great.

SUMMARY

In at least one embodiment, the present invention provides a device and/or a method for cooling X-radiation detectors, which can be embodied simply and which in particular are suitable for use in computer tomography systems.

A fundamental concept of the cooling device according to at least one embodiment of the invention is that the collimator plates of the X-radiation detector, which are used to reduce scattered radiation, may also be used advantageously for cooling the X-radiation detector. The cooling device according to at least one embodiment of the invention is now characterized in that the collimator plates are designed, and/or the cooling device comprises a ventilation device which is designed, so that the space between the collimator plates is at least partially exposed to a cooling air flow in order to cool the radiation detector.

Corresponding suitability of the collimator plates for the detector cooling according to at least one embodiment of the invention is obtained since they mostly include materials which, besides their radiation absorption property, also have good thermal conductivity. This applies in particular to the lead or tungsten collimated plates often used in practice. Furthermore, there is often in any case a highly thermally conductive connection between the collimator plates and the other components of an X-radiation detector, for example based on adhesive bonding, so that good heat transfer from the other detector components to the collimator plates is promoted.

By exposing the space between the collimator plates to cooling air, heat transfer from the collimator plates to the environment is reinforced so that cooling of the entire X-radiation detector is obtained effectively. Owing to the fact that the collimator plates are approximately aligned mutually parallel—for example with the conventional radial alignment at an X-ray source—the effectiveness of the cooling is promoted since an advantageous laminar cooling air flow can be induced, as also occurs for example when cooling semiconductor processors by the well-known metallic heat sinks with lamellar shaping.

In order to generate the cooling air flow, it is likewise conceivable for the shaping of the collimator plates to be supplemented so that air flowing past the radiation detector is deflected onto the spaces between the collimator plates, and the radiation detector heat is therefore transported away faster. As an alternative, the radiation detector may also be supplemented with a special ventilation device which generates a cooling air flow between the collimator plates.

Compared with the use of coolants, heat exchangers or fans integrated into the detectors, the cooling device according to at least one embodiment of the invention is distinguished in that it resorts to already existing properties and components of X-radiation detectors for the dissipation of heat. A corresponding embodiment of the cooling device is therefore economical, and also suitable for use in computer tomography systems which have a multiplicity of detectors.

The cooling device according to at least one embodiment of the invention can furthermore be integrated into a detector arrangement without substantially increasing the overall weight, so that the dynamic properties of X-ray systems with moving detector arrangements are unchanged, or are changed only to a tolerable extent.

The method according to at least one embodiment of the invention for cooling a radiation detector, having a detector surface and a plurality of collimator plates arranged in the direction of X-radiation before the detector surface, is achieved in that the space between the collimator plates is at least partially exposed to a cooling air flow.

Further advantageous configurations and refinements of the invention will be found in the dependent claims and the following description.

In an example embodiment of the cooling device according to the invention, the collimator plates are designed so that the cooling air flow is generated between the collimator plates by moving the radiation detector, for example by a rotational movement of the gantry of a computer tomography system. Inter alia, the often planar collimator plates may be supplemented with a vaned shape so that ambient air is conducted between the collimator plates by moving the detector. Similarly, the ventilation device in an advantageous configuration of the invention may be configured so that the cooling air flow is generated by moving the X-radiation detector.

In another configuration of at least one embodiment of the ventilation device, the ventilation device encloses a cavity and has an intake opening to receive cooling air and a feed opening to deliver cooling air into the space between the collimator plates. Advantageously, the ventilation device may in this case be designed so that the received cooling air is compressed and/or accelerated at the intake opening. This means that the cooling air has a relatively high flow rate at the feed opening, compared with the speed at the intake opening. The higher flow rate improves the efficiency of the cooling. A cavity with two openings and a funneled shape, the smaller opening facing the collimator plates, would be an example of such a ventilation device.

Since in general a cooling air flow received at the intake opening need not necessarily be already aligned in the direction of the principal extent plane of the collimator plates, in an example embodiment the ventilation device according to the invention has the property that it can deflect the cooling air flow. Thus, the ventilation device is arranged and/or designed so that the direction of the cooling air flow inside the intake opening differs from the direction of the cooling air flow inside the feed opening. Particularly for the case described above, in which the cooling air flow is generated by moving the X-radiation detector, such deflection is particularly advantageous since, for example, it also permits cooling devices in which the radiation detector is moved in a direction perpendicular to the principal extent plane of the collimator plates.

Besides the intake opening and the feed opening, the ventilation device according to at least one embodiment of the invention in another configuration has a bypass opening for further delivery of cooling air. The cooling air received at the intake opening is in this case divided so that a first part is sent through the feed opening into the space between the collimator plates and a second part is output through the bypass opening. This second part may then in turn be used to cool a further radiation detector or another component of an X-ray system.

The cooling device according to at least one embodiment of the invention may furthermore be characterized in that it includes an air discharge device, which is designed so that it receives at least a part of the cooling air flow introduced into the space between the collimator plates by the ventilation device. For example, this can advantageously prevent the heat absorbed between the collimator plates from being sent into regions of an X-ray system which exhibit sensitivity to heat. Furthermore, such an air discharge device can reinforce the flow of cooling air between the collimator plates, for example by a suction effect in the air discharge device. The suction effect might inter alia be induced by moving the radiation detector or by additional instruments, such as fans or pumps, integrated into the air discharge device. A particularly advantageous configuration of the cooling device according to at least one embodiment of the invention is obtained when the ventilation device and the air discharge device are arranged on opposite sides of the collimator plates.

Besides the generation of the cooling air flow by moving the radiation detector, the cooling air flow could also be induced by generating it outside the detector and bringing it to the detector by suitable instruments. For instance, it is conceivable for an X-ray system to be connected to a compressed air source, and for the compressed air to be sent via the cooling device according to at least one embodiment of the invention into the space between the collimator plates. Furthermore, in an example configuration of at least one embodiment of the invention, the ventilation device itself may comprise technical instruments such as fans or pumps, which generate a cooling air flow.

In addition to introducing cooling air into the space between the collimator plates, the ventilation device according to at least one embodiment of the invention may also be designed so that the image recorder or other instruments contained in the radiation detector, for example electronic circuits, are exposed to cooling air. The effectiveness of the cooling can thereby be improved, in particular because X-ray detectors contain not only a light sensor, for example photodiode arrays, but also other electronic circuits such as analog-digital converters, which give off power loss in the form of heat.

As described in the introduction, X-ray systems—and especially computer tomography systems—often comprise an arrangement of a plurality of radiation detectors. These may for example be arranged in the form of a so-called radiation detector rack, i.e. next to one another in a row. Radiation detector arrays are furthermore used, i.e. matricial arrangements of X-radiation detectors, particularly in order to permit short examination times. At least one embodiment of the present invention may advantageously be used for such arrangements of radiation detectors, particularly in computer tomography systems. In this case at least some of the radiation detectors have cooling devices according to at least one embodiment of the invention, which expose the space between the collimator plates of the radiation detectors inside the arrangement to cooling air.

In a matricial arrangement of the detectors, for example, the detector respectively lying at the edge of a row or column of the matrix may include a cooling device according to at least one embodiment of the invention, and thus supply cooling air to all detectors of the relevant row or column. The sum total of the cooling devices in a radiation detector arrangement will be referred to below by the term "cooling system". The cooling system according to the invention may be constructed so that the respective cooling instruments are assigned to the radiation detectors. This leads to a modular structure which, for example, is advantageous whenever several variants of a detector arrangement need to be manufactured, for instance different matrix configurations.

In an example embodiment of the cooling system, the ventilation devices of the cooling devices are arranged and/or designed so that all the radiation detectors are exposed to a cooling air flow with essentially the same strength. Such a configuration of the ventilation device is advantageous above all whenever the cooling air flow is induced by moving the detector arrangement, in particular by rotational movement of a detector arrangement of a computer tomography system, because this can prevent the detectors lying at the front in the movement direction from participating more strongly in the cooling air flow than the detectors which lie further behind— as seen in the direction of the movement. Disadvantageous strongly differing cooling of the individual detectors is correspondingly prevented.

In another example embodiment of the cooling system according to at least one embodiment of the invention, a cooling air channel is employed which encloses the ventilation devices and supplies them with cooling air. The cooling channel may also contain a pump or a fan, which generate the cooling air flow inside the cooling air channel.

A cooling system according to at least one embodiment of the invention may furthermore include cooling devices supplemented with a bypass opening as explained above, at least some of the respective cooling devices being arranged so that the intake opening of the ventilation device of a first radiation detector is arranged opposite the bypass opening of the ventilation device of a second, neighboring radiation detector. Some of the cooling air received by the ventilation device of the first detector is thus forwarded to the ventilation device of the second detector. Correspondingly, a plurality of detectors may be arranged next to one another in an advantageous modular fashion, a kind of cooling air channel being formed by the ventilation devices themselves.

The cooling device according to at least one embodiment of the invention and the cooling system according to at least one embodiment of the invention may generally be used in all X-ray systems which comprise radiation detectors with collimator plates.

Use in computer tomography systems is particularly advantageous—as mentioned above—since these are often characterized by a large number of X-radiation detectors and therefore a correspondingly great demand for dissipating the heat produced in the detectors. In computer tomography systems with a static detection arrangement, i.e. when using so-called "ring detector devices" or "inverse fan beam devices", the cooling air flow between the collimator plates may for example be generated by an external compressed air supply, fans or pumps.

Besides this, the cooling system according to at least one embodiment of the invention is suitable particularly for the computer tomography systems widespread in practice, in which the radiation detector arrangement is moved during the X-ray image recording. This also applies to "fan beam devices", which conventionally include a so-called gantry that has a support ring and encloses a usually circular examination space. Both the X-ray source and the radiation detector arrangement are located on the support ring of the gantry.

The gantry rotates during the X-ray image recording, i.e. the radiation detector arrangement rotates around the patient. This system-specific rotational movement may advantageously be utilized by the cooling system according to at least one embodiment of the invention, in order to generate a cooling air flow between the collimator plates for cooling the radiation detector arrangement.

In this method, the cooling air flow is optionally deflected or deviated in order to achieve better cooling of the collimator plates. The additional weight which is added to the gantry by the cooling system can be kept small owing to the relatively simple structure, so that the dynamic properties of the gantry are affected only little. It is furthermore to be assumed that the cooling system is less susceptible to faults and therefore more economical to operate, since elaborate mechanical instruments such as tube lines, coolant pumps or heat exchangers, can be obviated in many cases.

BRIEF DESCRIPTION OF THE DRAWINGS

The invention will be explained in more detail again below with reference to the appended figures with the aid of example embodiments.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

Figure 1:
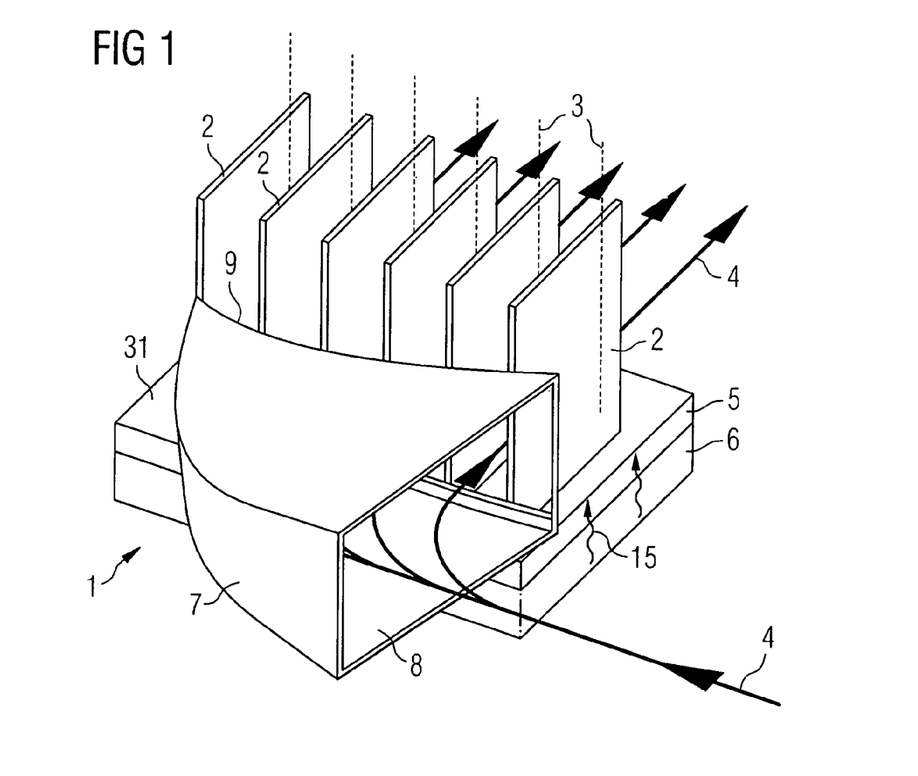
FIG. 1 shows a schematic representation of a radiation detector with a cooling device according to the invention according to a first example embodiment.

FIG. 1 shows a schematic representation of a radiation detector 1 with one embodiment of a cooling device according to an embodiment of the invention. The radiation detector 1 consists of a radiation converter 5, for example a scintillation crystal, and an image recorder 6 which is connected to the radiation converter 5. The image recorder 6 in a simple embodiment may be a single photodiode or a matrix including a plurality of photodiodes. It is furthermore conceivable that in other embodiments, the image recorder 6 also contains electrical circuits for selecting individual photodiodes or analog-digital converters.

A plurality of collimator plates 2 are arranged on the detector surface 31 facing the incident X-radiation 3. A ventilation device 7 according to an embodiment of the invention receives a cooling air flow 4 at an intake opening 8, deflects the cooling air flow 4 and outputs it via the feed opening 9 in the direction of the collimator plates 2. The space between the collimator plates 2 is thereby at least partially exposed to the cooling air flow 4. The cooling is thus achieved by the heat 15 produced in the radiation converter 5 and the image recorder 6 being forwarded to the collimator plates 2, which in turn dissipate the heat 15 to the cooling air flow 4.

FIG. 1 shows a simplified representation of a radiation detector 1 with a few collimator plates 2 arranged mutually parallel and a planar radiation converter 5 as well as a planar image recorder 6. The cooling device according to an embodiment of the invention, however, is also advantageously applicable for the often used radiation detectors 1 with an arc-shaped configuration of the radiation converter 5 and the image recorder 6. Such radiation detectors 1 are often used in computer tomography systems 21. The collimator plates 2 are then aligned radially in the direction of the X-ray source 25. Furthermore, typical radiation detectors 1 usually have a large number of collimator plates 2 in order to separate the individual detector channels from one another. For the sake of better clarity, however, only some of the collimator plates are indicated here.

Figure 2:
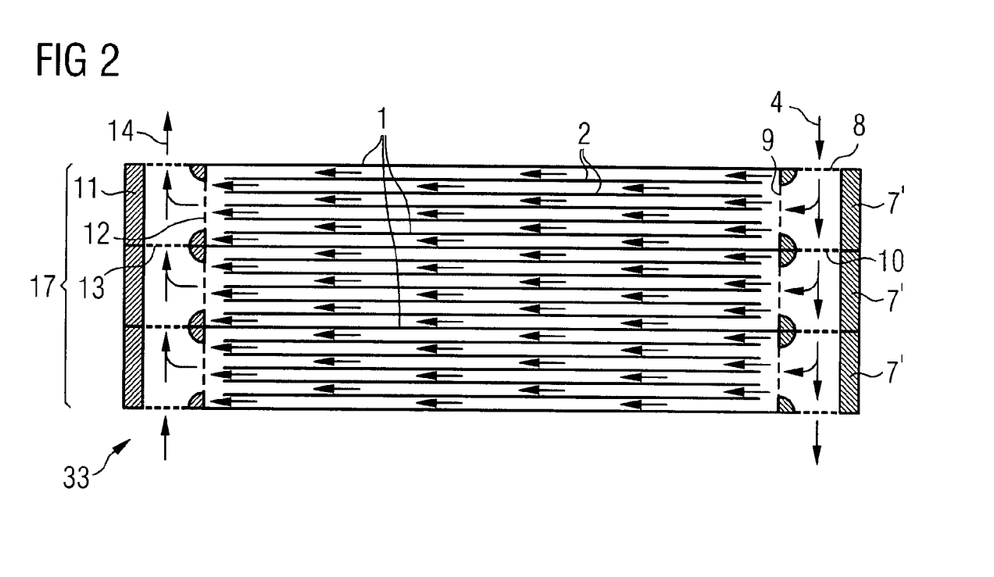
FIG. 2 shows a schematic representation of an example embodiment of a cooling system according to the invention for a radiation detector arrangement.

FIG. 2 shows a schematic representation of an example embodiment of a cooling system 33 according to the invention for a radiation detector arrangement 17, which is constructed here by way of example from three elongate radiation detectors 1 that are arranged next to one another in a direction perpendicular to the principal extent plane of the collimator plates 2. The radiation detectors 1 are respectively supplemented with a ventilation device 7' and an air discharge device 11. In the representation selected, the collimator plates 2 are arranged mutually parallel perpendicularly to the plane of the representation. The collimator plates 2 lie between the ventilation device 7' and the air discharge device 11.

A first part of the cooling air flow 4 received at the intake opening 8 of one of the ventilation devices 7' is partially output via the feed opening 9 into the space between the collimator plates 2. The remaining second part of the received cooling air flow 4, on the other hand, is delivered further via the bypass opening 13 into the ventilation device 7' of a neighboring radiation detector 1. The mutually connected ventilation devices 7' thus form a kind of cooling air channel, via which the cooling air flow 4 is distributed over the individual radiation detectors 1.

The air discharge devices 11 are arranged in a similar way. The cooling air flow 4 heated between the collimator plates 2 is received by discharge openings 12, optionally delivered further via a bypass opening 13, and output via a discharge opening 14. The represented embodiment of the cooling system 33 is distinguished by its modular structure, that is to say no specific adaptation is necessary for a particular number of radiation detectors 1 involved.

Figure 3A:
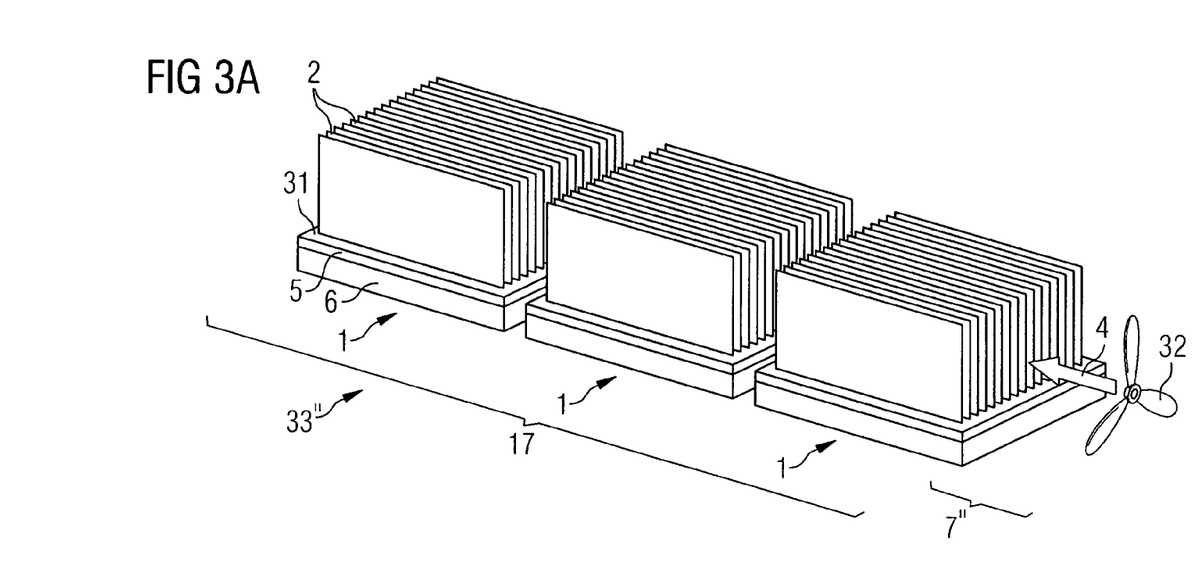
FIGS. 3A and 3B show schematic representations of another cooling system according to an example embodiment of the invention of a radiation detector arrangement.
Figure 3B:
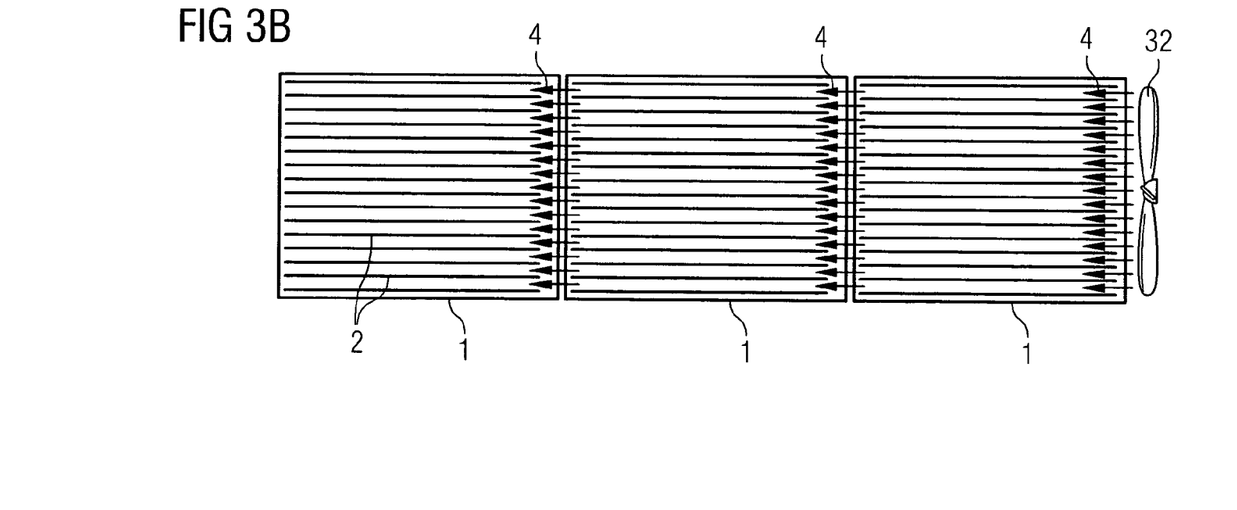

FIGS. 3A and 3B show highly abstract representations of another example embodiment of the cooling system 33" according to the invention of a radiation detector arrangement 17. Besides the perspective representation in FIG. 3A, FIG. 3B shows a view from above with collimator plates 2 lying perpendicular to the plane of the representation. The radiation detector arrangement 17 shown here includes, by way of example, three radiation detectors 1 arranged next to one another in the principal extent plane of the collimator plates 2.

The cooling air flow 4 between the collimator plates 2 in this embodiment of the invention is generated primarily by a fan 32. Owing to the alignment of the radiation detectors 1, it is not absolutely necessary for each radiation detector 1 to have a corresponding fan 32. The lamellar arrangement of the collimator plates 2 here advantageously reinforces the further delivery of the cooling air flow 4 from a radiation detector 1 placed near the fan to a neighboring radiation detector 1 lying further away from the fan.

Figure 4:
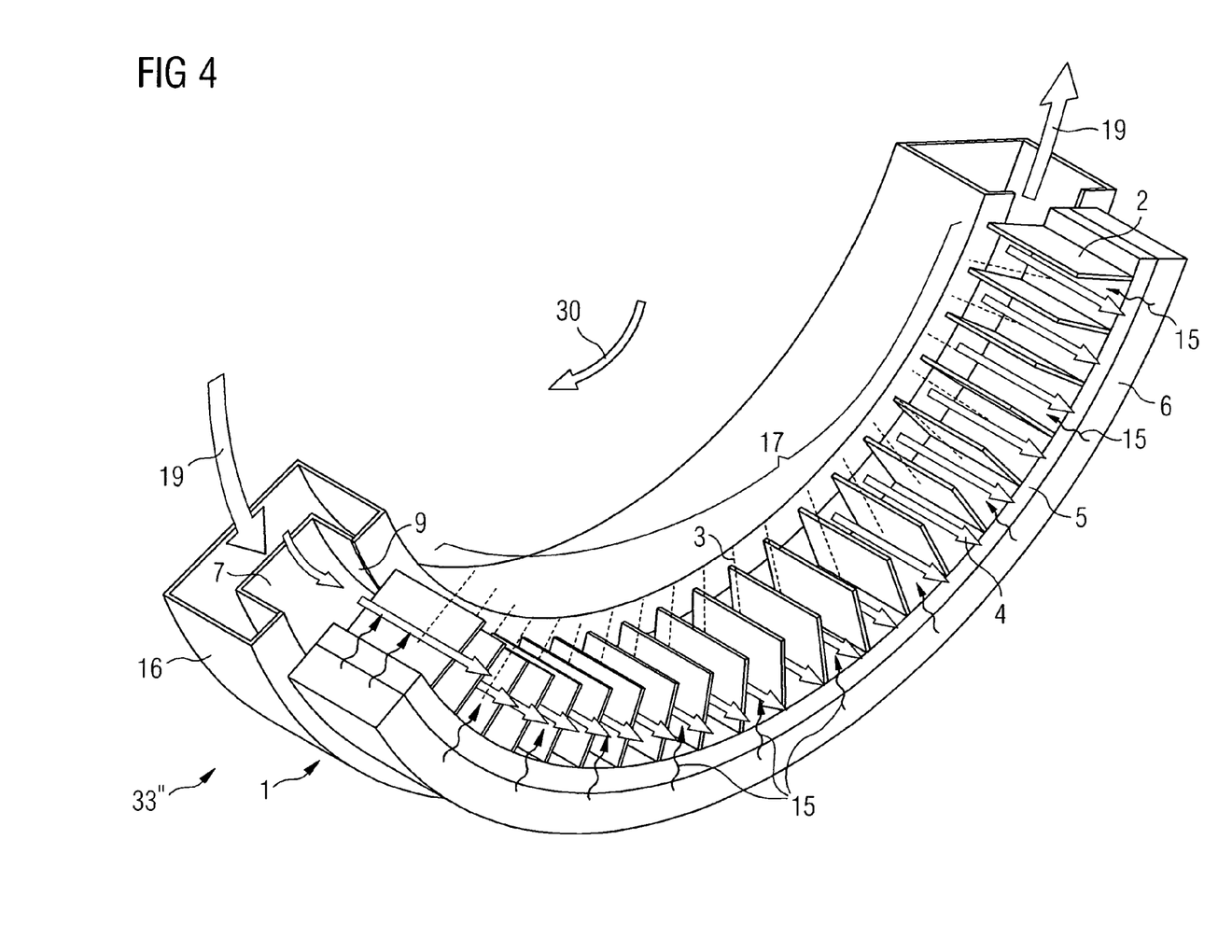
FIG. 4 shows a schematic representation of a cooling system according to an example embodiment of the invention with a cooling air channel for a radiation detector arrangement mounted in a mobile fashion with radially aligned collimator plates.

FIG. 4 shows a schematic representation of another configuration of the cooling system 33' according to an embodiment of the invention with a cooling air channel 16 for a radiation detector arrangement 17 mounted in a mobile fashion, which is characterized by radially aligned collimator plates 2. Such a radiation detector arrangement 17 is characteristic for the class of "fan beam devices" described above among computer tomography systems 21. For the sake of clarity, only relatively few collimator plates 2 are represented in FIG. 4. Currently conventional radiation detector arrangements 17 can have several hundred collimator plates 2, in order to separate the individual detector channels from one another. The distance between the collimator plates then may, for example, be only about 1 mm.

Figure 5:
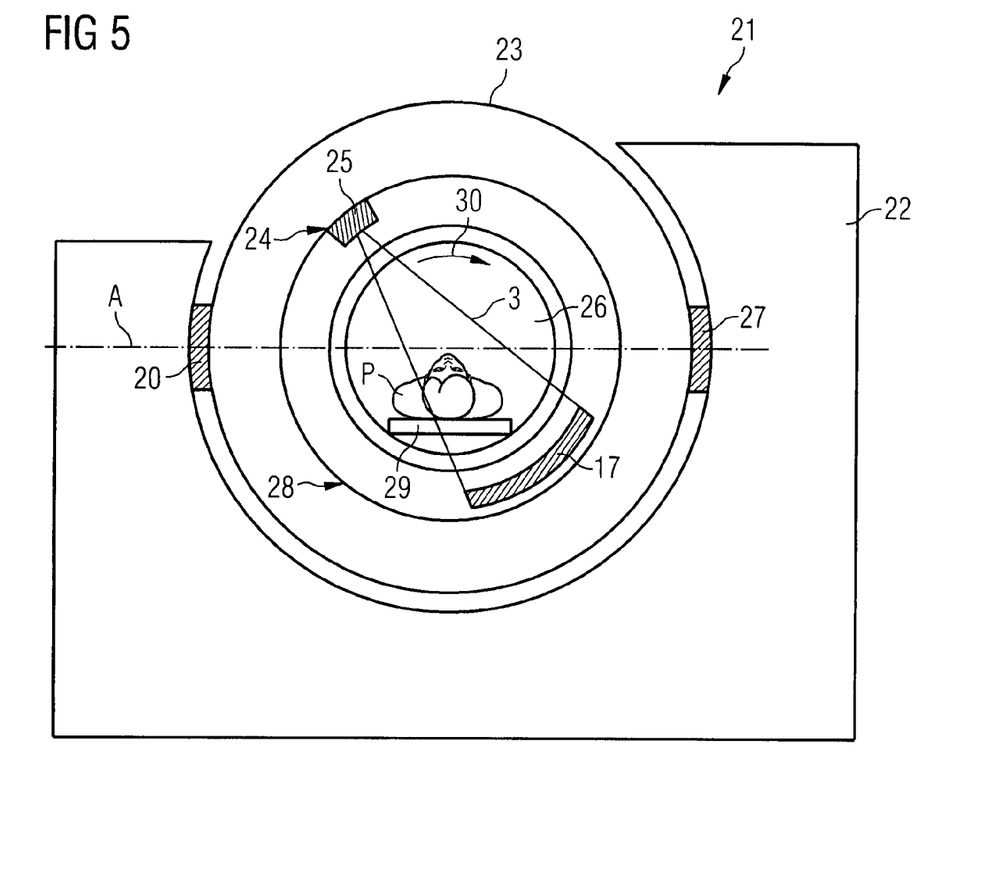
FIG. 5 shows a schematic cross section through the gantry housing of a computer tomography system.

FIG. 5 shows a schematic cross section through the gantry housing 23, mounted so that it can tilt via coaxial bearings 20 in a gantry base 22, of a corresponding version of a computer tomography system 21 frequently encountered in medical practice. The rotatably mounted support ring 28 of the gantry 24 includes an X-ray source 25, from which X-radiation 3 is emitted with a fanned alignment. The radiation detector arrangement 17 arranged radially opposite the X-ray source 25, on the support ring 28, receives the X-radiation 3 after it has passed through the patient P lying on a table 29 in the examination space 26. During the X-ray image recording, the rotational movement 30 of the gantry 24 generates a cooling air flow 19 inside the cooling air channel 16. The cooling air channel 16 contains ventilation devices 7, not represented in detail in FIG. 4 for the sake of clarity, which deflect the cooling air flow 19 into the gaps between the collimator plates 2.

Such a cooling air channel 16 may however also be used in computer tomography systems 21 with static radiation detector arrangements 17, in which case the cooling air flow 4, 19 may for example be produced by a pump or a fan 32.

Lastly, it should once more be pointed out that the cooling devices and methods for cooling a radiation detector as described above are example embodiments, which may be modified in a wide variety of ways by experts in the technical field without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A cooling device for a radiation detector having a detector surface and a plurality of collimator plates arranged in the direction of X-radiation before the detector surface, wherein at least one of,
   the collimator plates are designed so that the space between the collimator plates is at least partially exposed to a cooling air flow to cool the radiation detector, and
   the cooling device includes a ventilation device, the ventilation device being designed so that the space between the collimator plates is at least partially exposed to a cooling air flow to cool the radiation detector.

2. The cooling device as claimed in claim 1, wherein the radiation detector is mounted in a mobile fashion, and wherein at least one of the collimator plates are designed, and the ventilation device is designed so that the cooling air flow is generated at least partially by moving the radiation detector.

3. The cooling device as claimed in claim 2, wherein the ventilation device includes an intake opening to receive cooling air and a feed opening to deliver cooling air into the space between the collimator plates.

4. The cooling device as claimed in claim 1, wherein the ventilation device includes an intake opening to receive cooling air and a feed opening to deliver cooling air into the space between the collimator plates.

5. The cooling device as claimed in claim 4, wherein the ventilation device is designed so that the received cooling air is at least one of compressed and accelerated.

6. The cooling device as claimed in claim 5, wherein the ventilation device is at least one of arranged and designed so that the direction of the cooling air flow inside the intake opening differs from the direction of the cooling air flow inside the feed opening.

7. The cooling device as claimed in claim 4, wherein the ventilation device is at least one of arranged and designed so that the direction of the cooling air flow inside the intake opening differs from the direction of the cooling air flow inside the feed opening.

8. The cooling device as claimed in claim 4, wherein the ventilation device includes a bypass opening for further delivery of the cooling air flow, so that a first part of the cooling air received via the intake opening is sent through the feed opening into the space between the collimator plates and a second part is output through the bypass opening.

9. A cooling system for a radiation detector arrangement including a plurality of radiation detectors arranged next to one another, the cooling system comprising a plurality of cooling devices for a radiation detector having a detector surface and a plurality of collimator plates arranged in the direction of X-radiation before the detector surface, wherein at least one of,
   the collimator plates are designed so that the space between the collimator plates is at least partially exposed to a cooling air flow to cool the radiation detector, and
   the cooling device includes a ventilation device, the ventilation device being designed so that the space between the collimator plates is at least partially exposed to a cooling air flow to cool the radiation detector, the cooling system further comprising a multiplicity of cooling devices as claimed in claim 6, arranged so that for at least some of the radiation detectors, the intake opening of the ventilation device is arranged next to the bypass opening of the ventilation device of the neighboring radiation detector.

10. The cooling device as claimed in claim 1, further comprising an air discharge device, designed to receive at least a part of the cooling air flow introduced into the space between the collimator plates by the ventilation device.

11. The cooling device as claimed in claim 10, wherein the ventilation device and the air discharge device are arranged on opposite sides of the collimator plates.

12. The cooling device as claimed in claim 1, wherein the ventilation device includes at least one of a fan and a pump.

13. The cooling device as claimed in claim 1, wherein the radiation detector includes a radiation converter arranged next to the collimator plates and an image recorder, arranged on the other side of the radiation converter from the collimator plates, and wherein the ventilation device is designed to expose the image recorder at least partially to a cooling air flow.

14. A cooling system for a radiation detector arrangement including a plurality of radiation detectors arranged next to one another, the cooling system comprising a plurality of cooling devices as claimed in claim 1, assigned to the individual radiation detectors.

15. The cooling system as claimed in claim 14, wherein the ventilation devices of the cooling devices are at least one of arranged and designed so that all the radiation detectors are exposed to a cooling air flow with essentially the same strength.

16. The cooling system as claimed in claim 14, wherein a cooling air channel encloses the ventilation devices of the radiation detectors.

17. The cooling system as claimed in claim 16, wherein the cooling air channel includes at least one of a fan and a pump for generating a cooling air flow inside the cooling channel.

18. A computer tomography system having a radiation detector arrangement and a cooling system as claimed in claim 14.

19. The computer tomography system as claimed in claim 18, wherein the cooling system is at least one of arranged and designed so that the cooling air flow is generated at least partially by a rotational movement of the radiation detector arrangement.

20. The cooling system of claim 1, wherein the plurality of collimator plates are arranged in a direction perpendicular to a rotation direction of the detector surface and parallel to a direction of the cooling air flow in the space between the plurality of collimator plates.

21. A method for cooling a radiation detector including a detector surface and a plurality of collimator plates arranged in the direction of X-radiation before the detector surface, comprising:

at least partially exposing the space between the collimator plates to a cooling air flow by a ventilation device.

22. The method as claimed in claim 21, wherein the cooling air flow is generated at least partially by moving the radiation detector.

23. The method as claimed in claim 22, wherein, in order to cool a plurality of radiation detectors of a radiation detector arrangement in a computer tomography system, the cooling air flow is generated at least partially by a rotational movement of the radiation detector arrangement.

24. A radiation detector, comprising:
a detector surface; and
a plurality of collimator plates arranged in the direction of X-radiation before the detector surface, wherein at least one of
the collimator plates is designed so that the space between the collimator plates is at least partially exposed to a cooling air flow to cool the radiation detector, and
the cooling device includes a ventilation device, the ventilation device being designed so that the space between the collimator plates is at least partially exposed to a cooling air flow to cool the radiation detector.

25. The cooling device as claimed in claim 24, wherein the radiation detector is mounted in a mobile fashion, and wherein at least one of the collimator plates are designed, and the ventilation device is designed so that the cooling air flow is generated at least partially by moving the radiation detector.

26. The cooling device as claimed in claim 24, wherein the ventilation device includes an intake opening to receive cooling air and a feed opening to deliver cooling air into the space between the collimator plates.

27. The cooling device as claimed in claim 26, wherein the ventilation device is designed so that the received cooling air is at least one of compressed and accelerated.

28. The cooling device as claimed in claim 24, further comprising an air discharge device, designed to receive at least a part of the cooling air flow introduced into the space between the collimator plates by the ventilation device.

29. The cooling device as claimed in claim 28, wherein the ventilation device and the air discharge device are arranged on opposite sides of the collimator plates.

30. A cooling system for a radiation detector arrangement including a plurality of radiation detectors arranged next to one another, the cooling system comprising a plurality of cooling devices as claimed in claim 24, assigned to the individual radiation detectors.

* * * * *